United States Patent
Araci et al.

(10) Patent No.: US 10,085,637 B2
(45) Date of Patent: Oct. 2, 2018

(54) CONTACT LENS WITH A MICROFLUIDIC CHANNEL TO MONITOR RADIUS OF CURVATURE OF CORNEA

(71) Applicants: Ismail Emre Araci, Palo Alto, CA (US); Murat Baday, Menlo Park, CA (US)

(72) Inventors: Ismail Emre Araci, Palo Alto, CA (US); Murat Baday, Menlo Park, CA (US)

(73) Assignee: SMARTLENS, INC., Santa Clara, CA (US)

( * ) Notice: Subject to any disclaimer, the term of this patent is extended or adjusted under 35 U.S.C. 154(b) by 424 days.

(21) Appl. No.: 15/067,378

(22) Filed: Mar. 11, 2016

(65) Prior Publication Data
US 2016/0262616 A1    Sep. 15, 2016

Related U.S. Application Data

(60) Provisional application No. 62/131,429, filed on Mar. 11, 2015.

(51) Int. Cl.
*A61B 3/16*    (2006.01)
*A61B 3/107*    (2006.01)

(52) U.S. Cl.
CPC ............... *A61B 3/16* (2013.01); *A61B 3/107* (2013.01)

(58) Field of Classification Search
CPC .. A61B 3/16; A61B 3/107; G02C 7/04–7/049
USPC ............... 351/159, 247, 159.02, 159.73, 178
See application file for complete search history.

(56) References Cited

U.S. PATENT DOCUMENTS

| | | | | |
|---|---|---|---|---|
| 9,964,780 | B2 * | 5/2018 | Pugh | G02C 7/049 |
| 9,977,258 | B2 * | 5/2018 | Pugh | G02C 7/049 |
| 2004/0169932 | A1 * | 9/2004 | Esch | A61F 2/16 |
| | | | | 359/665 |
| 2014/0343387 | A1 * | 11/2014 | Pugh | A61B 5/6821 |
| | | | | 600/365 |
| 2015/0164321 | A1 * | 6/2015 | Weibel | A61B 3/16 |
| | | | | 600/405 |

* cited by examiner

Primary Examiner — William R Alexander
Assistant Examiner — Grant Gagnon

(57) ABSTRACT a contact lens that monitors the radius of curvature of cornea includes an amplification chamber, am annular membrane, a microfluidic channel, and a gas reservoir within a top and bottom lens layers of the contact lens. The annular membrane is positioned within the amplification chamber and is in fluid communication with the gas reservoir through the microfluidic channel. A working gas within the gas reservoir and a working fluid within the amplification chamber and the microfluidic channel create a fluid-gas equilibrium pressure interface. The curvature change of the cornea results the amplification chamber wall and the annular membrane to deflect, wherein the deflection results the fluid-gas equilibrium pressure interface baseline to change within the microfluidic channel. Then the baseline position change is recorded by an external imaging system to analysis sensitivity calculation of the cornea.

20 Claims, 10 Drawing Sheets

CONTACT LENS WITH A MICROFLUIDIC CHANNEL TO MONITOR RADIUS OF CURVATURE OF CORNEA

The current application claims a priority to the U.S. Provisional Patent application Ser. No. 62/131,429 filed on Mar. 11, 2015.

FIELD OF THE INVENTION

The present invention relates generally to an apparatus for a contact lens. More specifically, the present invention is a contact lens that monitors the radius of curvature of cornea with an integrated microfluidic channel.

BACKGROUND OF THE INVENTION

Glaucoma is characterized by a progressive loss of retinal ganglion cells, a characteristic optic neuropathy and patterns of visual field loss in the more advanced stages. Even though glaucoma can be caused by many different risk factors, the increased intraocular pressure (IOP) is identified as the main risk factor of glaucoma. As a result, doctors often require continuous monitoring of the IOP for effective treatment of glaucoma. The change of IOP causes a change in the radius of curvature of the cornea as the aforementioned mechanical change can be used as an indication of the IOP. Current methods to measure the radius of corneal curvature require expensive electrical components and connections. Even though most patients get tested once a year during their eye-exams, patients at risk of increase IOP require continuous monitoring of the change of IOP. The existing methods of measuring the radius of curvature require electrical connections and radio frequency components, raising safety concerns and making them uncomfortable and expensive. Additionally, the high cost of these devices does not allow long term monitoring of radius of curvature changes. Even though some existing contact lenses are able to measure the IOP through a microfluidic channel, these contact lenses lack the required lifetime, which is greater than 24 hours, to be used as a practical device. The reason that the existing contact lenses lack the required lifetime is the permeability of the Polydimethylsiloxane (PDMS) that causes a gas leak. Another problem with the existing contact lenses is the surface energy of the sensing liquid is not taken into consideration. As a result, the high surface energy of the sensing liquid causes high capillary pressure drop that causes non-linear sensor behavior.

It is an objective of the present invention is to provide a contact lens with a microfluidic channel to monitor radius of curvature of the cornea with high sensitivity, high linearity, and with long lifetime. The present invention includes a microfluidic channel that converts the changes in the radius of corneal curvature into gas/liquid interface movement inside the microfluidic channel. Then the movement of gas/liquid interface can be optically detected by utilizing an external imaging system that includes components such as a camera, a lens, a microscope and a light source. As a result, the present invention provides a low cost contact lens that can be daily worn by the patients over the years of treatment. The present invention also greatly improves the effectiveness of glaucoma treatment which typically is for the lifetime of the patient.

DETAIL DESCRIPTIONS OF THE INVENTION

All illustrations of the drawings are for the purpose of describing selected versions of the present invention and are not intended to limit the scope of the present invention.

Figure 1:
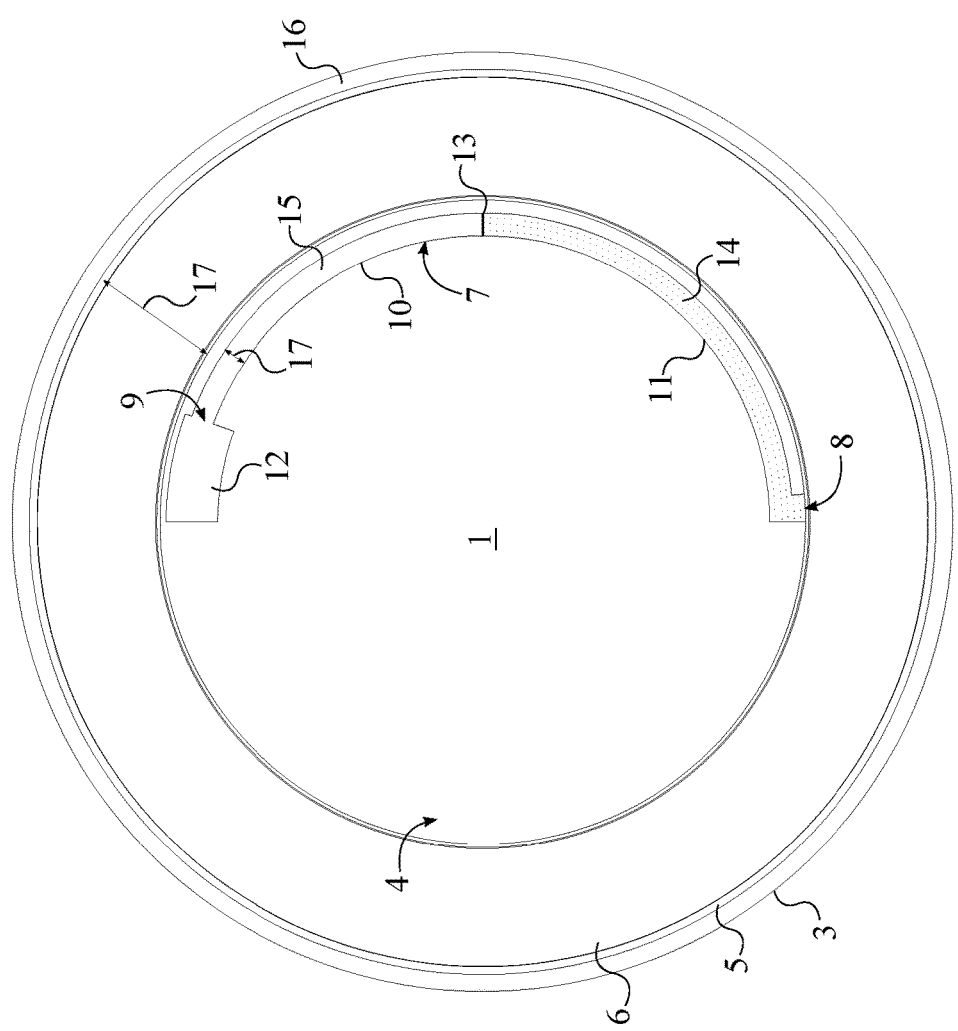
FIG. 1 is a front schematic view of the present invention.

The present invention is a contact lens that monitors the radius of curvature of the cornea. Since the increase intraocular pressure (IOP) is one of the main risk factors that causes glaucoma, continuous monitoring of IOP is necessary for effective treatments instead of periodic monitoring of IOP. As shown in FIG. 1, the present invention comprises a top lens layer 1, a bottom lens layer 2, an amplification chamber 5, an annular membrane 6, a microfluidic channel 7, and a gas reservoir 12. In reference to the general configuration of the present invention, the top lens layer 1 and the bottom lens layer 2 are concentrically connected to each other in order to delineate the amplification chamber 5, the microfluidic channel 7, and the gas reservoir 12. The annular membrane 6 is perimetrically positioned within the amplification chamber 5 to detect a change in the radius of curvature of the cornea within the present invention. Then the change in the radius of curvature of the cornea can be shown through a fluid-gas equilibrium pressure interface 13 that is generated within the microfluidic channel 7. More specifically, the position changes of the fluid-gas equilibrium pressure interface 13 provide a direct correlation to the change in the radius of curvature of the cornea as the microfluidic channel 7 is in fluid communication with the gas reservoir 12. A baseline position of the fluid-gas equilibrium pressure interface 13 and any changes to the baseline position are recorded using an external imaging system in order to perform sensitivity calculations for the cornea. The present invention can be placed on one or both of the eyes of the patient.

Figure 10:
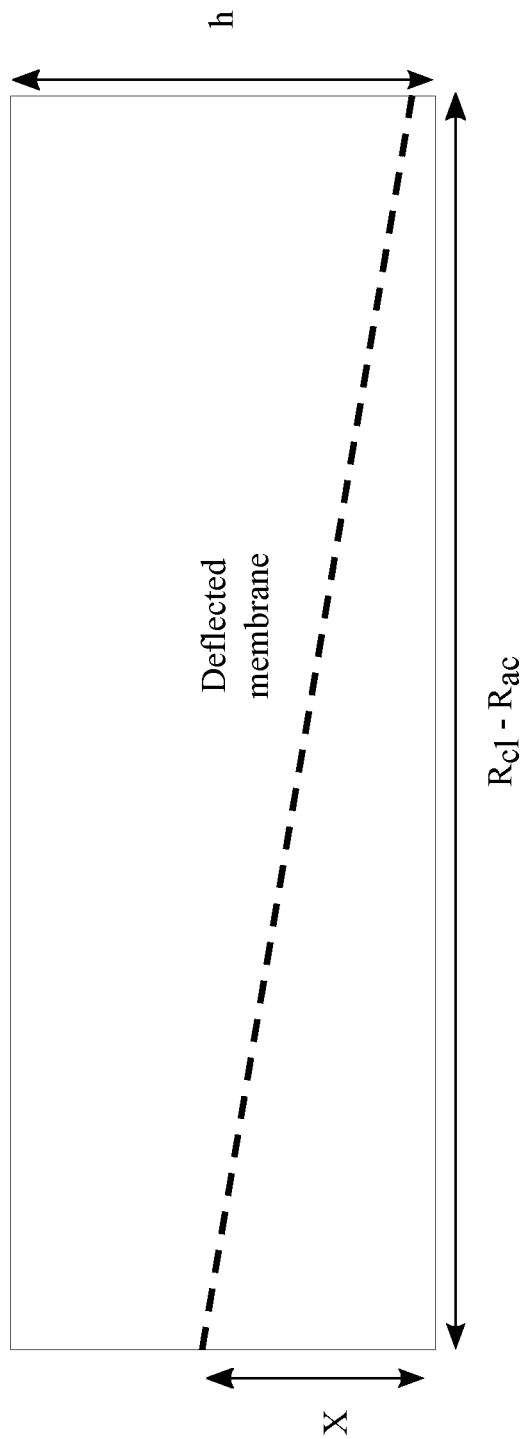
FIG. 10 is a reference diagram for the sensitivity calculation of the present invention.

The contact lens is preferably made of a polymer or any other type of material that includes increased oxygen permeability, lens wettability, and overall comfort. In reference to FIG. 1, the microfluidic channel 7 and the gas reservoir 12 are positioned within a central region 4 of the top lens and the bottom. The microfluidic channel 7 and the gas reservoir 12 is made of non-gas-permeable materials, such as glass, ceramics, metals, epoxies, Parylene-C, etc. The central region 4 is radially enclosed by the amplification chamber 5 and the annular membrane 6 so that the microfluidic channel 7 is able to display an accurate reading for the fluid-gas equilibrium pressure interface 13 with the amplification chamber 5. More specifically, a first open end 8 of the microfluidic channel 7 is in fluid communication with the amplification chamber 5 and the annular membrane 6. A second open end 9 of the microfluidic channel 7, which is oppositely positioned of the first open end 8 along the microfluidic channel 7, is in fluid communication with the gas reservoir 12. As a result, the microfluidic channel 7 is able to complete a hermetic connection between the amplification chamber 5 and the gas reservoir 12. The top lens layer 1 may have a different Young's modulus than the bottom contact lens 2. In reference to a preferred embodiment of the present invention, the bottom lens layer 2 is softer compare to the top lens layer 1 as the bottom lens layer 2 has lower Young's modulus compare to the top lens layer 1. The difference between the Young's modulus can be adjusted to ensure the volume changes of the amplification chamber 5, as shown in FIG. 10, when the radius of curvature of the contact lens changes.

The microfluidic channel 7 is preferably configured to a height of 50 micron and a width of 50 micron. The gas reservoir 12 is preferably configured with dimensions 1 mm by 1 mm by 1 mm. However, the microfluidic channel 7 and the gas reservoir 12 are not limited the aforementioned dimensions and can vary according different embodiment of the present invention. The microfluidic channel 7 and the gas reservoir 12 can be coated with a low gas permeability film to create hermetic sealing if necessary. The amplification chamber 5 is preferably made of elastomeric polymer that can deflect in response to the change in the radius of curvature of the cornea.

In reference to FIG. 1, a working fluid 14 is distributed from the amplification chamber 5 to the fluid-gas equilibrium pressure interface 13 through the first open end 8. As a result, a fluid-region 11 of the microfluidic channel 7 is established from the first open end 8 to the fluid-gas equilibrium pressure interface 13. The working fluid 14 is preferably a low surface tension compound, such as perfluorocarbon, so that the working liquid is able to verify low capillary pressure drop at the fluid-gas equilibrium pressure interface 13. A working gas 15 should have a low solubility in the working liquid 14 and is distributed from the gas reservoir 12 to the fluid-gas equilibrium pressure interface 13 through the second open end 9. As a result, a gas-region 10 of the microfluidic channel 7 is established from the second open end 9 to the fluid-gas equilibrium pressure interface 13. The microfluidic channel 7 and the gas reservoir 12 may include various sizes and shapes to accommodate different treatment process and to calculate advance changes in the radius of curvature of the cornea.

The changes in the radius of curvature of the cornea cause a deflection of the walls of the amplification chamber 5 as the working fluid 14 is filled within the amplification chamber 5. The amplification chamber 5 then transfers the deflection of the walls to the annular membrane 6. The deflection of the amplification chamber 5 and the annular membrane 6 subsequently displace the working fluid 14 toward the microfluidic channel 7. Since the amplification chamber 5 and the annular member are positioned around the contact lens, a small deflection of the walls is able to maximize the displacement of working fluid 14 within the present invention. The displaced volume of working fluid 14 then moves toward the gas reservoir 12, causing the fluid-gas equilibrium pressure interface 13 to move in the direction of the gas reservoir 12. The gas reservoir 12 should be sealed to prevent gas leakage. Then the movement of the fluid-gas equilibrium pressure interface 13 can be detected from the external imaging system to conduct sensitivity calculations of the contact lens.

Figure 11:
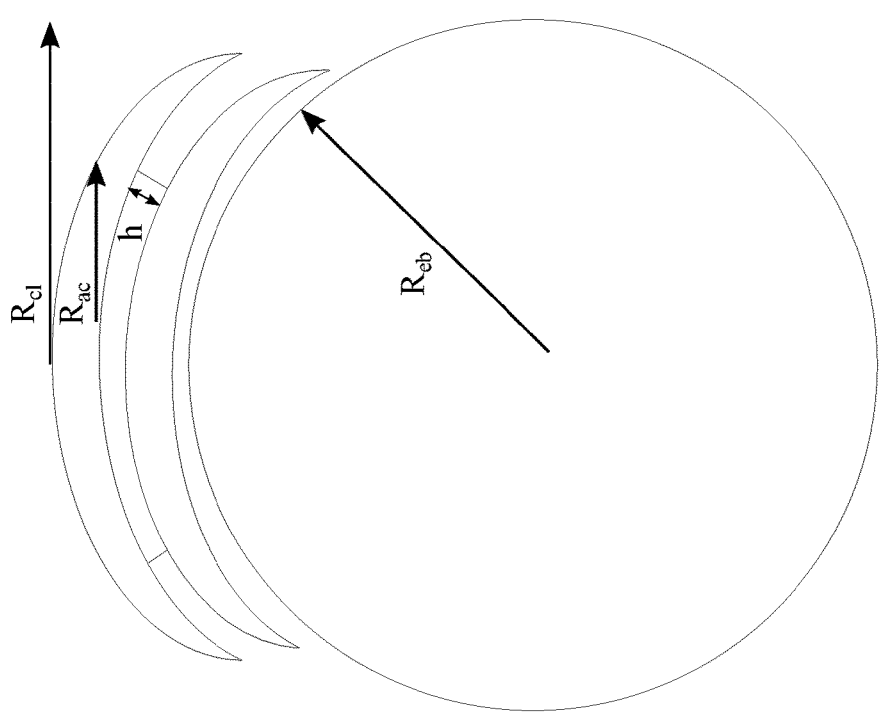
FIG. 11 is another reference diagram for the sensitivity calculation of the alternative embodiment of the present invention.
Figure 12:
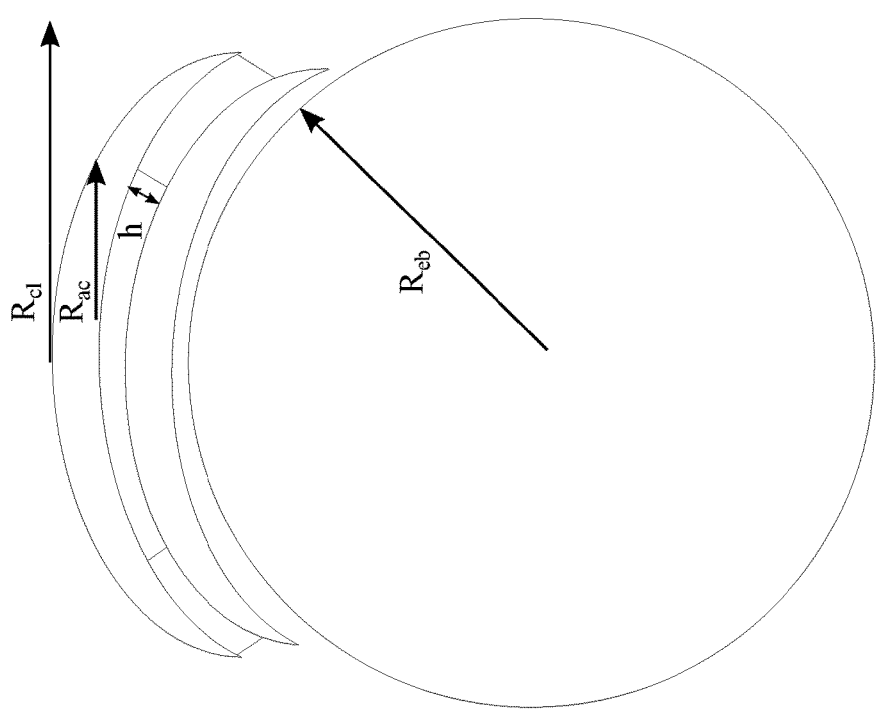
FIG. 12 is another reference diagram for the sensitivity calculation of the preferred embodiment of the present invention.

In reference to FIG. 10-FIG. 12, the sensitivity calculation of the contact lens may comprise the following general process. However, additional assumptions, equations, and parameters may be required to fully implement the sensitivity calculation through the present invention. Assuming each 1 millimeter of mercury (mmHg) IOP change causes a dR micrometer radius of curvature change of the eye. For an adult with the radius of an eyeball ($R_{eb}$), for a contact lens sensor with a radius ($R_{cl}$), and the amplification chamber 5 radius ($R_{ac}$), the volume of amplification chamber 5 can be expressed by this following formula:

$$V_{ac} = 2\pi \times h \times R_{cl} \times (R_{cl} - R_{ac})$$

assuming all angles are small. The amplification chamber 5 can be drawn as a rectangle where the annular membrane 6 deflects due to the IOP changes as shown in FIG. 10.

The deflection, x can be calculated by the following formula:

$$x = \frac{R_{cl} dR}{2\pi R_{eb}}$$

Then the volume reduction due to the deflection is:

$$dV = \frac{R_{cl} dR}{2 R_{eb}} (R_{cl} - R_{ac}) R_{cl}$$

Then the resulting amplification chamber 5 volume is:

$$V_{ac}^{final} = \left(1 - \frac{R_{cl} dR}{4\pi h R_{eb}}\right) V_{ac}$$

From the well-known relation $P_{init} \times V_{init} = P_{final} \times V_{final}$. The final pressure in the amplification chamber 5 becomes;

$$P_{final} = \left(\frac{4\pi h R_{eb}}{4\pi h R_{eb} - R_{cl} dR}\right) P_{init}$$

As the lens radius ($R_{cl}$) increases, the $P_{final}$ also increases where the geometrical amplification factor dependents on the lens radius ($R_{cl}$). When the initial gas pressure inside the gas reservoir 12 is assumed as 1 atmospheric pressure (760 mmHg), the sensitivity of the contact lens is defined as the displacement of the fluid-gas equilibrium pressure interface 13 in response to 1 mmHg pressure change in the eye. This can be derived from the following formula:

$$S = \frac{1}{761} \times \frac{V_{res}}{A_{ch}}\left(1 + \frac{V_{ch}}{V_{res}}\right)\frac{R_{cl}dR}{4\pi hR_{eb} - R_{cl}dR}$$

where $V_{res}$, $A_{ch}$, and $V_{ch}$ are gas reservoir 12 volume, channel cross section, and channel volume respectively. In reference to FIG. 11 and FIG. 12, when gas reservoir 12 volume is much greater than the channel volume, and dR is much smaller than h the sensitivity is proportional to:

$$S \sim \frac{V_{res}}{A_{ch}} \frac{R_{ch}dR}{hR_{eb}}$$

Figure 2:
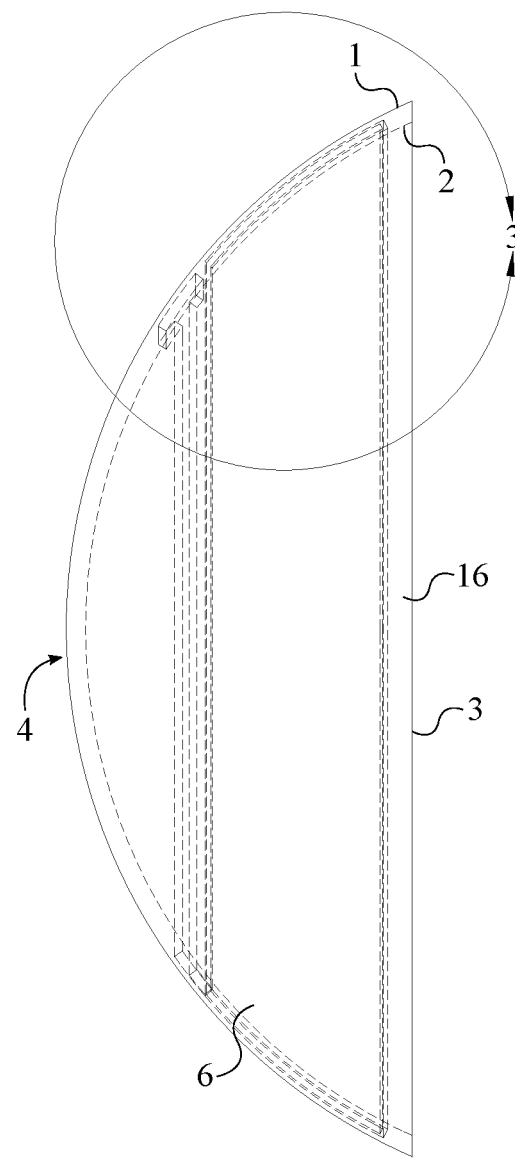
FIG. 2 is a side view of the preferred embodiment of the present invention, showing a circular section taken shown in FIG. 3.
Figure 3:
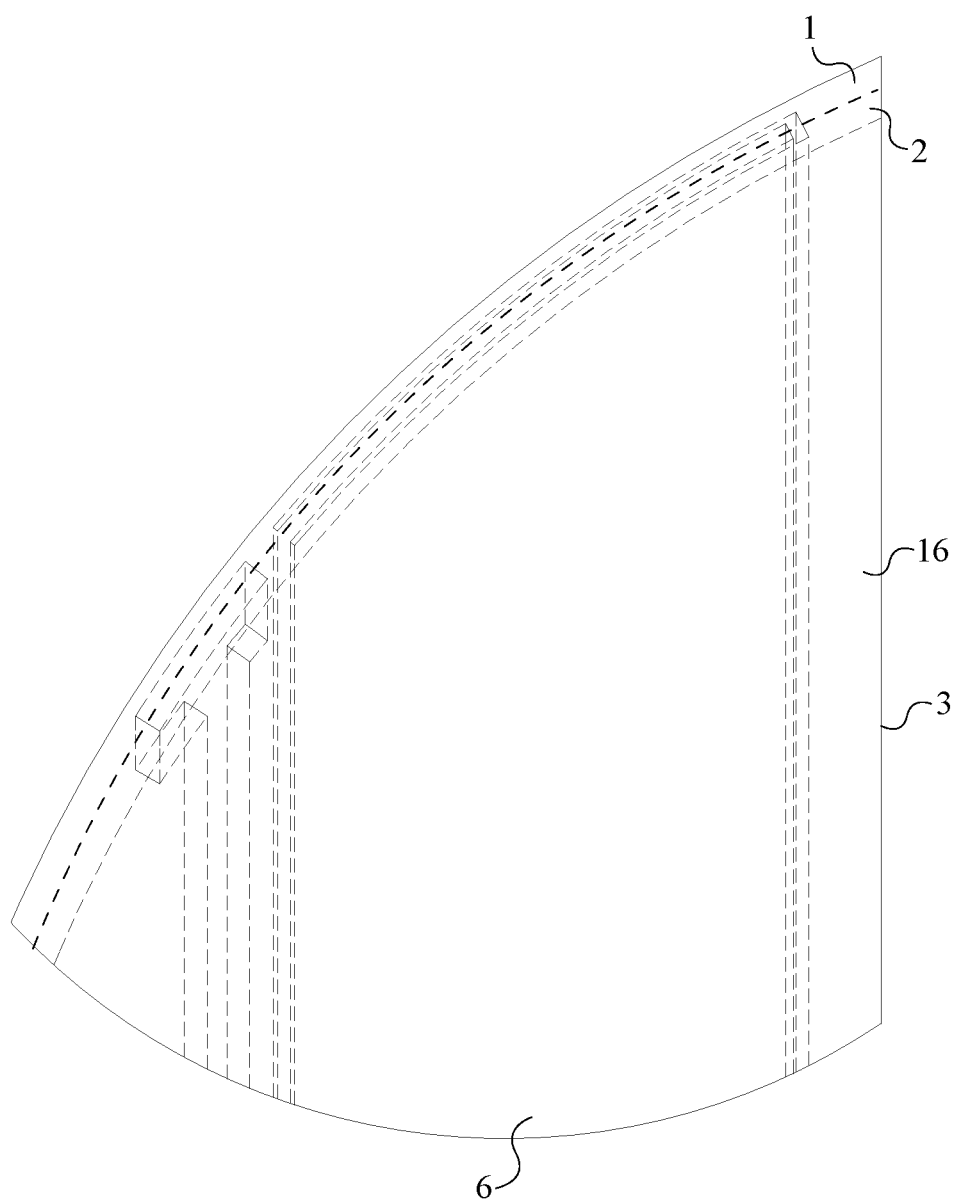
FIG. 3 is a detailed view of the preferred embodiment of the present invention taken within the circular section of FIG. 2.

In reference to FIG. 1-3 that shows a preferred embodiment of the present invention, the top lens layer 1 and the bottom lens layer 2 further comprise an edge 3. The edge 3 of the top lens layer 1 is perimetrically connected to the edge 3 of the bottom lens layer 2 to delineate a hermetic seal 16. Then the amplification chamber 5 is radially extended from the central region 4 of the top lens layer 1 and the bottom lens layer 2 to the hermetic seal 16, wherein the preferred embodiment forms a closed-ended configuration.

Figure 4:
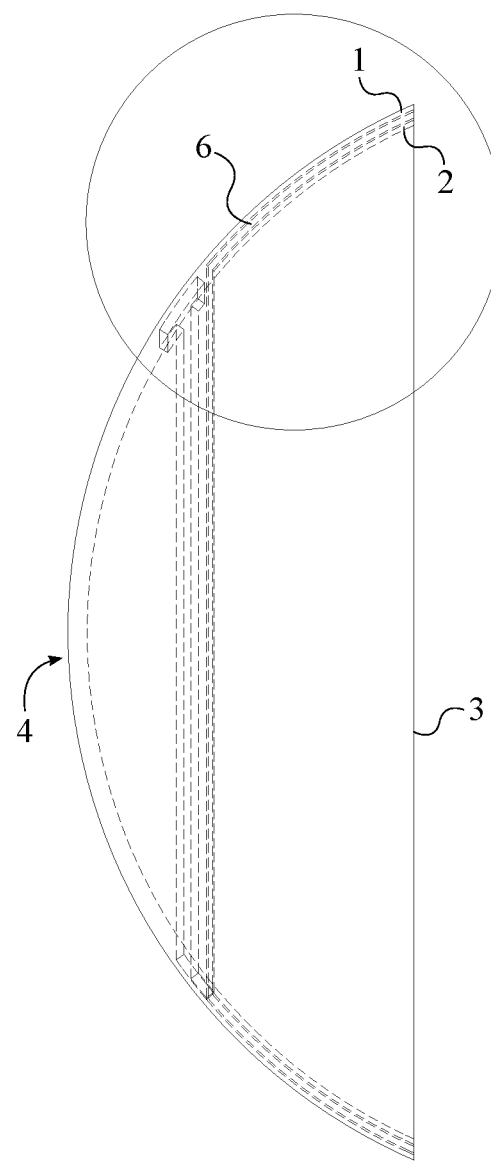
FIG. 4 is a side view of the alternative embodiment of the present invention, showing a circular section taken shown in FIG. 5.
Figure 5:
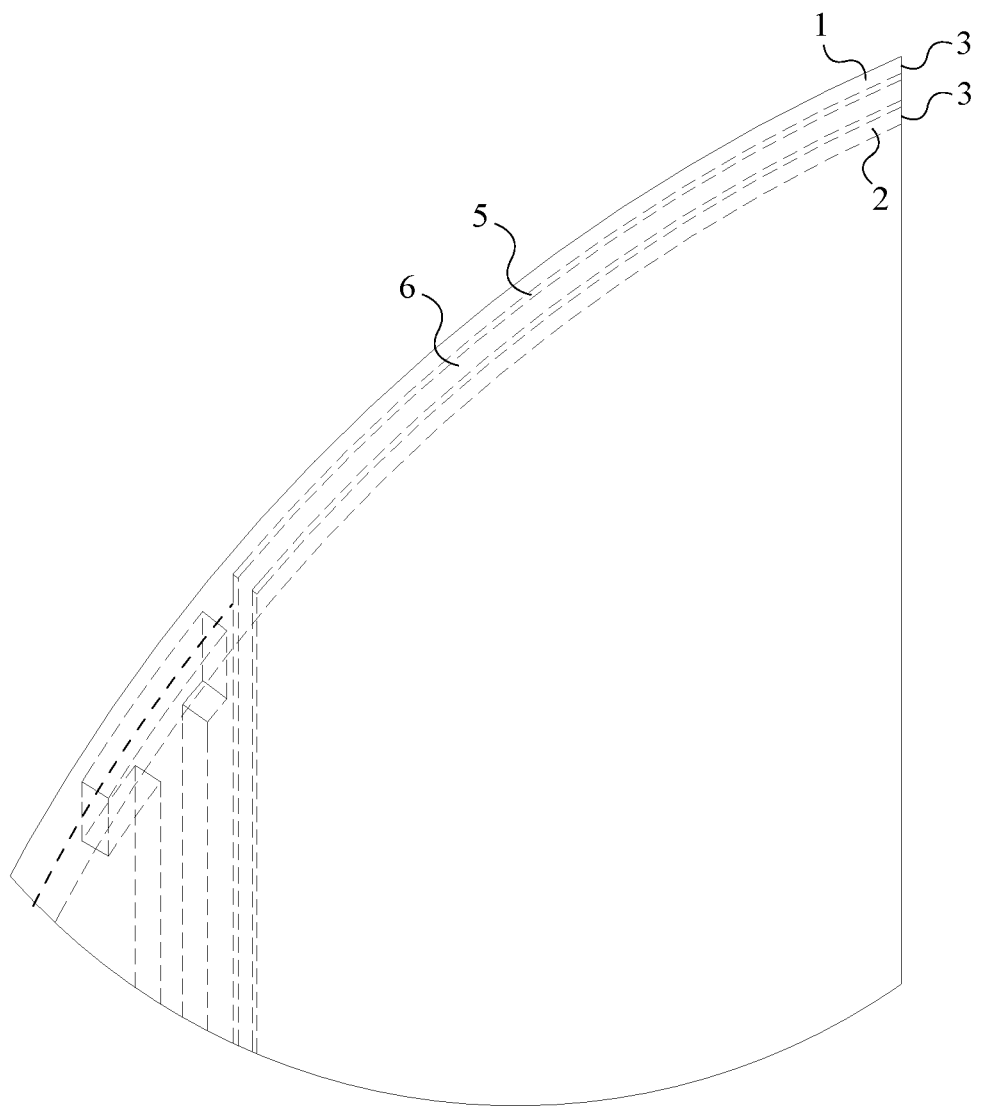
FIG. 5 is a detailed view of the alternative embodiment of the present invention taken within the circular section of FIG. 4.

In reference to FIG. 4-5 that shows an alternative embodiment of the present invention, the edge 3 of the top lens layer 1 is positioned offset from the edge 3 of the bottom lens layer 2. Additionally, the edge 3 of the top lens layer 1 is positioned coplanar with the edge 3 of the bottom lens layer 2. As a result, the amplification chamber 5 is radially extended from the central region 4 of the top lens layer 1 and the bottom lens layer 2 to the edge 3 of the top lens layer 1 and the bottom lens layer 2, wherein the alternative embodiment forms an opened-ended configuration. The opened-ended configuration also requires selective modification to the amplification chamber 5 so that the surface energy is able to retain the working fluid 14 within the amplification chamber 5 and the fluid-region 11.

In reference to the preferred embodiment and the alternative embodiment, the amplification chamber 5 is positioned as close as possible to the edge 3 of the top lens layer 1 and the bottom lens layer 2. The amplification chamber 5 is also positioned outside of the microfluidic channel 7. Additionally, a diameter 17 of the amplification chamber 5 is larger than a diameter 17 of the microfluidic channel 7.

There are three general methods of manufacturing the present invention. As for the first method, the amplification chamber 5, the gas reservoir 12, and the microfluidic channel 7 can be hot embossed/engraved/machined into the top lens layer 1 and/or the bottom lens layer 2. Then the annular membrane 6 is positioned within the amplification chamber 5, where the top lens layer 1 and the bottom lens layer 2 are bonded together to complete the present invention. As for the second method, the amplification chamber 5, the gas reservoir 12, and the microfluidic channel 7 are fabricated using soft lithography into the top lens layer 1 and/or the bottom lens layer 2 Similar to first method, the annular membrane 6 is positioned within the amplification chamber 5 and the top lens layer 1 and the bottom lens layer 2 are bonded together to complete the present invention. As for the third method, the amplification chamber 5, the gas reservoir 12, and the microfluidic channel 7 are made separately using polymer capillary tubes and chambers. Then the annular membrane 6 is inserted into the amplification chamber 5. The amplification chamber 5, the gas reservoir 12, and the microfluidic channel 7 are then embedded or attached to the existing contact lens. Even though the manufacturing process is described according three different methods, the present invention can utilize any other type of efficient manufacturing methods as long as the functionality of the present invention is not compromised during the manufacturing process.

Figure 7:
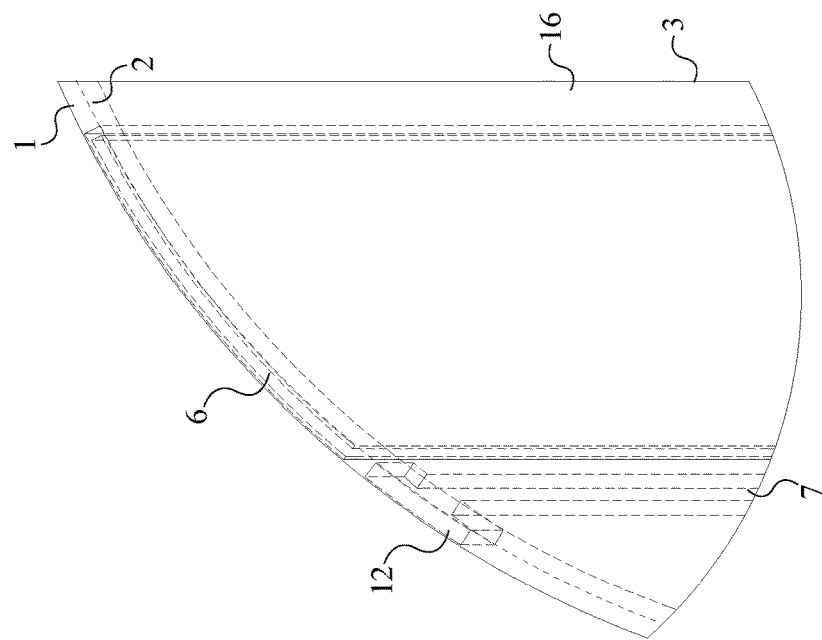
FIG. 7 is a detailed sectional view from FIG. 6, showing the amplification chamber, the microfluidic channel, and the gas reservoir.
Figure 6:
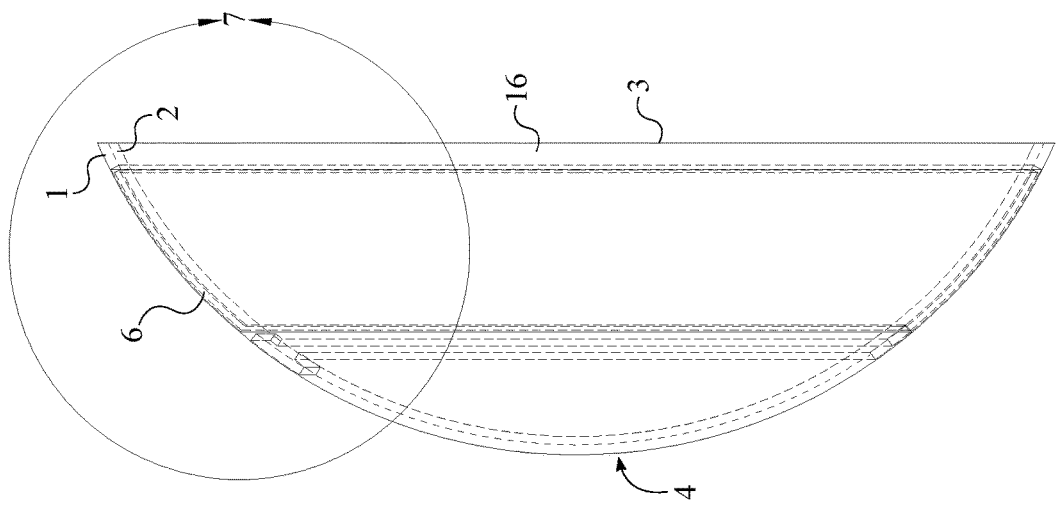
FIG. 6 is a side view of the present invention, wherein the amplification chamber, the microfluidic channel, and the gas reservoir are integrated into the top lens layer.
Figure 9:
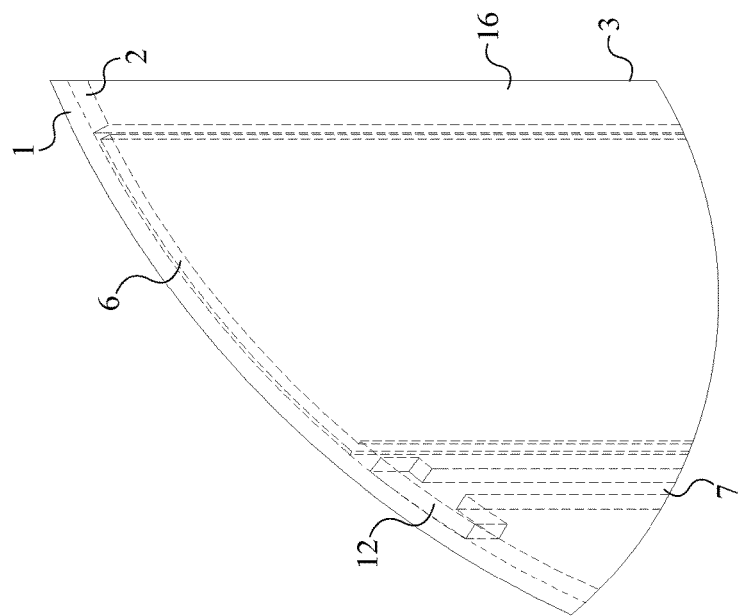
FIG. 9 is a detailed sectional view from FIG. 8, showing the amplification chamber, the microfluidic channel, and the gas reservoir.
Figure 8:
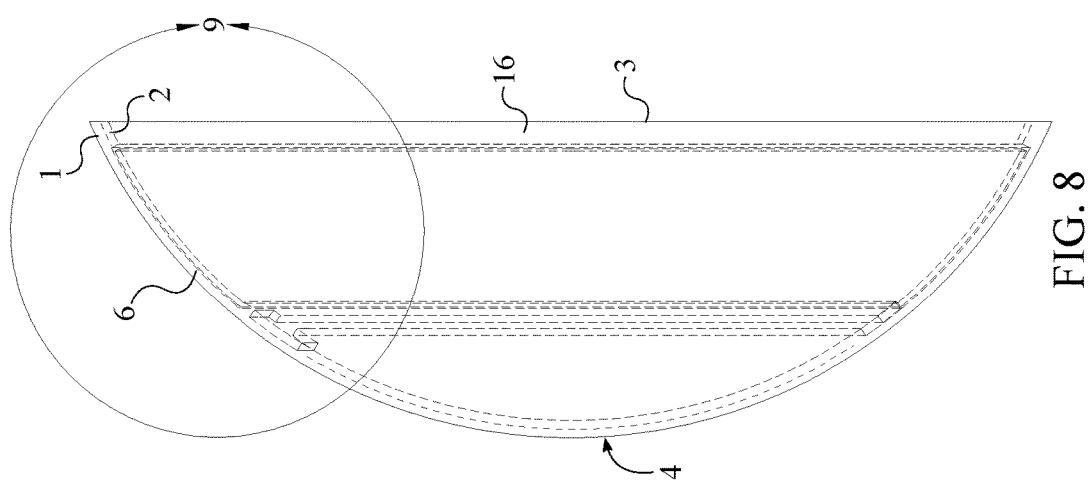
FIG. 8 is a side view of the present invention, wherein the amplification chamber, the microfluidic channel, and the gas reservoir are integrated into the bottom lens layer.

The present invention can have different configurations for the placement of the components, where one does not precede the other. In reference to FIG. 1-3, the amplification chamber 5, the microfluidic channel 7, and the gas reservoir 12 are integrated into the top lens layer 1 as the bottom lens layer 2 completes the first configuration of the present invention. In reference to FIG. 8-9, the amplification chamber 5, the microfluidic channel 7, and the gas reservoir 12 are integrated into the bottom lens layer 2 so that the top lens layer 1 can complete the second configuration of the present invention. In reference to FIG. 6-7, the amplification chamber 5, the microfluidic channel 7, and the gas reservoir 12 are integrated into the top lens layer 1 and the bottom lens layer 2, where the top lens layer 1 and the bottom lens layer 2 complete the third configuration of the present invention.

The present invention is a simple, non-invasive, and low cost method of measuring the change in the radius of curvature of the cornea. The sensitivity calculation can also be process through a mobile application of a smart phone in order to the improve the feasibility of the present invention. The present invention can be used wherever pressure effects on a surface have to be measured, such as blood pressure on the veins and arteries. The present invention can also be uses in avionics and mechanics application to calculate pressure effects on a surface.

Although the invention has been explained in relation to its preferred embodiment, it is to be understood that many other possible modifications and variations can be made without departing from the spirit and scope of the invention as hereinafter claimed.

What is claimed is:

1. A contact lens to monitor radius of curvature of the cornea comprises;
   a top lens layer;
   a bottom lens layer;
   an amplification chamber;
   an annular membrane;
   a microfluidic channel;
   a gas reservoir;
   the top lens layer and bottom lens layer being concentrically connected to each other to delineate the amplification chamber, the microfluidic channel, and the gas reservoir;
   the annular membrane being perimetrically positioned within the amplification chamber;
   the microfluidic channel and the gas reservoir being positioned within a central region of the top lens layer and the bottom lens layer;
   a first open end of the microfluidic channel being in fluid communication with the amplification chamber and the annular membrane; and
   a second open end of the microfluidic channel being in fluid communication with the gas reservoir, opposite of the first open end.

2. The contact lens to monitor radius of curvature of the cornea as claimed in claim 1 comprises;
   the top lens layer and the bottom lens layer further comprises an edge;
   the edge of the top lens layer being positioned offset from the edge of the bottom lens layer;
   the edge of the top lens layer being positioned coplanar with the edge of the bottom lens layer;

the amplification chamber being radially extended from the central region of the top lens layer and the bottom lens layer to the edge of the top lens layer and the bottom lens layer; and the amplification chamber being adjacently positioned with the edge of the top lens layer and the bottom lens layer.

3. The contact lens to monitor radius of curvature of cornea as claimed in claim 1, wherein a diameter of the amplification chamber is larger than a diameter of the microfluidic channel.

4. The contact lens to monitor radius of curvature of cornea as claimed in claim 1, wherein the amplification chamber, the microfluidic channel, and the gas reservoir being integrated into the top lens layer.

5. The contact lens to monitor radius of curvature of the cornea as claimed in claim 1, wherein the amplification chamber, the microfluidic channel, and the gas reservoir being integrated into the bottom lens layer.

6. The contact lens to monitor radius of curvature of the cornea as claimed in claim 1, wherein the amplification chamber, the microfluidic channel, and the gas reservoir being integrated into the top lens layer and the bottom lens layer.

7. The contact lens to monitor radius of curvature of the cornea as claimed in claim 1 comprises;
   a fluid-gas equilibrium pressure interface;
   a working fluid being distributed from the amplification chamber to the fluid-gas equilibrium pressure interface through the first open end; and
   a working gas being distributed from the gas reservoir to the fluid-gas equilibrium pressure interface through the second open end.

8. The contact lens to monitor radius of curvature of the cornea as claimed in claim 7, wherein a fluid-region of the microfluidic channel is established from the first open end to the fluid-gas equilibrium pressure interface.

9. The contact lens to monitor radius of curvature of the cornea as claimed in claim 7, wherein a gas-region of the microfluidic channel is established from the second open end to the fluid-gas equilibrium pressure interface.

10. The contact lens to monitor radius of curvature of the cornea as claimed in claim 1 comprises;
    the top lens layer and the bottom lens layer further comprises an edge;
    the edge of the top lens layer being perimetrically connected to the edge of the bottom lens layer to delineate a hermetic seal;
    the amplification chamber being radially extended from the central region of the top lens layer and the bottom lens layer to the hermetic seal; and
    the amplification chamber being adjacently positioned with the edge of the top lens layer and the bottom lens layer.

11. The contact lens to monitor radius of curvature of the cornea as claimed in claim 10, wherein the bottom lens layer has a lower young's modulus compare to the top lens layer.

12. A contact lens to monitor radius of curvature of the cornea comprises;
    a top lens layer;
    a bottom lens layer;
    an amplification chamber;
    an annular membrane;
    a microfluidic channel;
    a gas reservoir;
    a fluid-gas equilibrium pressure interface;

the top lens layer and bottom lens layer being concentrically connected to each other to delineate the amplification chamber, the microfluidic channel, and the gas reservoir;

the annular membrane being perimetrically positioned within the amplification chamber;

the microfluidic channel and the gas reservoir being positioned within a central region of the top lens layer and the bottom lens layer;

a first open end of the microfluidic channel being in fluid communication with the amplification chamber and the annular membrane;

a second open end of the microfluidic channel being in fluid communication with the gas reservoir, opposite of the first open end;

a working fluid being distributed from the amplification chamber to the fluid-gas equilibrium pressure interface through the first open end; and a working gas being distributed from the gas reservoir to the fluid-gas equilibrium pressure interface through the second open end.

13. The contact lens to monitor radius of curvature of the cornea as claimed in claim 12, wherein a fluid-region of the microfluidic channel is established from the first open end to the fluid-gas equilibrium pressure interface.

14. The contact lens to monitor radius of curvature of the cornea as claimed in claim 12, wherein a gas-region of the microfluidic channel is established from the second open end to the fluid-gas equilibrium pressure interface.

15. The contact lens to monitor radius of curvature of the cornea as claimed in claim 12 comprises;
    the top lens layer and the bottom lens layer further comprises an edge;
    the edge of the top lens layer being perimetrically connected to the edge of the bottom lens layer to delineate a hermetic seal;
    the amplification chamber being radially extended from the central region of the top lens layer and the bottom lens layer to the hermetic seal; and
    the amplification chamber being adjacently positioned with the edge of the top lens layer and the bottom lens layer.

16. The contact lens to monitor radius of curvature of the cornea as claimed in claim 12 comprises;
    the top lens layer and the bottom lens layer further comprises an edge;
    the edge of the top lens layer being positioned offset from the edge of the bottom lens layer;
    the edge of the top lens layer being positioned coplanar with the edge of the bottom lens layer;
    the amplification chamber being radially extended from the central region of the top lens layer and the bottom lens layer to the edge of the top lens layer and the bottom lens layer; and
    the amplification chamber being adjacently positioned with the edge of the top lens layer and the bottom lens layer.

17. The contact lens to monitor radius of curvature of cornea as claimed in claim 12, wherein a diameter of the amplification chamber is larger than a diameter of the microfluidic channel.

18. The contact lens to monitor radius of curvature of the cornea as claimed in claim 12, wherein the amplification chamber, the microfluidic channel, and the gas reservoir being integrated into the top lens layer.

19. The contact lens to monitor radius of curvature of the cornea as claimed in claim 12, wherein the amplification chamber, the microfluidic channel, and the gas reservoir being integrated into the bottom lens layer.

20. The contact lens to monitor radius of curvature of the cornea as claimed in claim 12, wherein the amplification chamber, the microfluidic channel, and the gas reservoir being integrated into the top lens layer and the bottom lens layer.

* * * * *